United States Patent
Dror et al.

[11] Patent Number: 5,102,402
[45] Date of Patent: Apr. 7, 1992

[54] RELEASABLE COATINGS ON BALLOON CATHETERS

[75] Inventors: Michael Dror, Edina; Paul Trescony, Robbinsdale, both of Minn.

[73] Assignee: Medtronic, Inc., Minneapolis, Minn.

[21] Appl. No.: 637,436

[22] Filed: Jan. 4, 1991

[51] Int. Cl.⁵ .................. A61M 5/32; A61M 29/00
[52] U.S. Cl. ........................... 604/265; 604/96
[58] Field of Search ............ 604/96, 99, 101, 265, 604/266, 51–53

[56] References Cited

U.S. PATENT DOCUMENTS

| 3,971,385 | 7/1976 | Corbett | 604/96 |
| 4,141,364 | 2/1979 | Schultze | 604/96 |
| 4,417,576 | 11/1983 | Baran | 604/101 |
| 4,423,725 | 1/1984 | Baran et al. | 604/101 |
| 4,603,152 | 7/1986 | Laurin et al. | 604/265 |
| 4,769,013 | 9/1988 | Lorenz et al. | 604/265 |
| 4,784,647 | 11/1988 | Gross | 604/264 |
| 4,839,175 | 6/1989 | Guo et al. | 424/450 |
| 4,923,450 | 5/1990 | Maeda et al. | 604/265 |
| 5,049,131 | 9/1991 | Deuss | 606/194 |

FOREIGN PATENT DOCUMENTS

| 0035036 | 10/1979 | Japan | 604/265 |
| 8912478 | 12/1989 | PCT Int'l Appl. | 604/104 |
| 2112646 | 7/1983 | United Kingdom | 604/265 |

Primary Examiner—C. Fred Rosenbaum
Assistant Examiner—Sharon Finkel

[57] ABSTRACT

Balloon catheters are prepared to include a coating of body affecting chemicals on the exterior of the balloon. The coating releases from the balloon when the balloon is inflated into contact with the lumen to be treated. The device provides accurate placement of the dosage required at the location in need of treatment.

21 Claims, 1 Drawing Sheet

RELEASABLE COATINGS ON BALLOON CATHETERS

BACKGROUND OF THE INVENTION

1. Field of the Invention

This invention relates to balloon catheters and more particularly to balloon angioplasty catheters having plaque-affecting compound releasably attached to the balloon wall.

2. Description of the Related Art

Dilatation balloons on catheters are well known in the art and are used to decrease the restriction caused by plaque within a vessel wall. Plaque varies greatly in consistency and may be anything from a soft fatty tissue to a harder calcified material. In either case, it is often desirable to do more than simply force a balloon against the plaque or other restriction in the hopes that any plaque and vessel wall may be stretched to open the lumen more fully. Laser angioplasty uses lasers to vaporize the plaque at the stenosis.

Researchers are currently screening a number of drugs to limit or dissolve plaque. Unfortunately, such compositions have been difficult to apply directly where needed. Instead, such drugs tend to be applied systemically which essentially treats portions of the body which need no treatment. Also, such treatments mean that the dosage to the body must be quite high to insure that the area having a need for treatment will receive adequate drugs.

Researchers at the University of Chicago School of Medicine incorporated a drug with magnetite particles in albumin solution and formed microcapsules 1.5 $\mu$m in diameter. The microcapsules were localized with the use of external magnetic fields. The local effects obtained matched those obtained with one hundred times as much drug given intravenously. J. Widder et al, *Adv. Pharm. Chemother.*, 16, 213 (1979).

Concentrated heparin is delivered by a perforated balloon catheter in work by Wolinsky et al, as described in European Patent publication 0 383 429 of C.R. Bard, Inc. The drug is sprayed through minute holes in the balloon. Also see JACC Vol. 15, No. 2, February 1990:475-81 by Wolinsky et al.

The assignee of the present invention has filed a patent application entitled "Intralumenal Drug Eluting Prosthesis", Ser. No. 07/486,580, filed Feb. 28, 1990 which places a stent bearing drug at the location desired. While potentially very useful, this procedure leaves a stent in position. In contrast, balloon angioplasty is accomplished within minutes and leaves no device in the vessel.

Other attempts have involved an application of catheters having two separated balloons and the introduction of the drug from an internal lumen of the catheter to the space formed between two inflated balloons. Obviously, this procedure requires the introduction of drug through a lumen within the catheter meaning that the volume of the drug is quite high. Also, if the plaque is badly fissured there will not be a complete seal between the two balloons and the drug will escape to other parts of the body through the vessel.

The art described in this section is not intended to constitute an admission that any patent, publication or other information referred to herein is "prior art" with respect to this invention, unless specifically designated as such. In addition, this section should not be construed to means that a search has been made or that no other pertinent information as defined in 37 C.F.R. § 1.56(a) exists.

SUMMARY OF THE INVENTION

The invention provides means for placing plaque-affecting drugs or diagnostic materials exactly where it is needed, and only where it is needed. The invention allows the modification of any existing balloon catheter by applying drugs to the exterior of the balloon. The drug may be applied to the balloon in the form of microcapsules, polymer coated crystals, a drug or other reservoir-bearing drug which may be adhered permanently or temporarily to the balloon wall. The term "drug" as used herein refers to any agent or combination of agents that may affect the cells in the lumen, and includes diagnostic reagents.

Generally, the drug or other bio-affecting chemical is placed in a reservoir formed from a polymer which may be coated over the wall of the balloon. The polymer may be attached to the balloon by solvent bonding, adhesives, welding or the like. If the balloon has folds, corrugations, cusps or the like, the polymer may be coated on to the balloon, inflated such that when the balloon deflates, large portions of the closed folds or other convolutions will entrap drug-containing polymer. Thus, the microcapsules may be mechanically trapped to the exterior of the balloon without the use of adhesives. The catheter is then guided to the appropriate position using conventional techniques. When the balloon is inflated, it expands greatly causing the polymer-coated drug to come in contact with the plaque or vessel wall and especially fills any fissures which may be present in the plaque. The drug in highly concentrated form is then placed exactly where it is needed. The actual dosage is extremely small since it must only effect the affected region.

The invention allows a physician to determine the type and extent of the plaque and then either use a previously coated catheter or to coat an uncoated catheter with a drug or drugs desired at the dosage indicated. Any balloon catheter may be modified by placing a coating of drug bearing reservoirs onto the wall of the balloon prior to its use. Since far less pressure is needed to rupture a microcapsule than to expand a lumen, the balloon may be of a simpler construction than with existing angioplasty balloons.

BRIEF DESCRIPTION OF THE DRAWINGS

A detailed description of the invention is hereafter described with specific reference being made to the drawings in which.

DESCRIPTION OF THE PREFERRED EMBODIMENTS

Drugs

Figure 1:
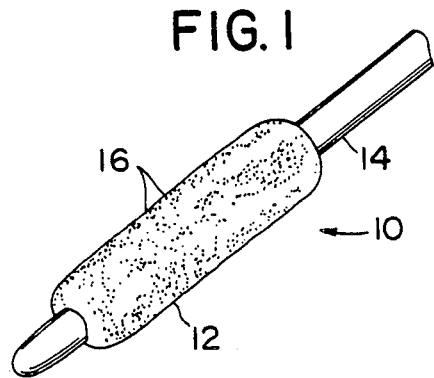
FIG. 1 is a fragmentary perspective view of an uninflated catheter of the invention.

The drugs in the microcapsules may be of any type which would be useful in treating the lumen. By treatment, the invention also contemplates diagnostic techniques which will aid in later treatment. Thus "drugs" may include diagnostic agents such as radiopaque compounds that allow the vessel to be visualized by fluoroscopy or similar methods. A dye within the microcapsules would be visible on the plaque after release by fluoroscopy. Also, the balloon itself may indicate the degree of blockage since only those microcapsules abutting against hard blockage will rupture, giving a reverse image of the blocked lumen.

In order to prevent restenosis in blood vessels, migration and subsequent proliferation of smooth muscle cells must be checked. Platelet aggregation and adhesion can be controlled with antiplatelets and anticoagulants. Growth factor and receptor blockers and antagonists may be used to limit the normal repair response. The drugs may be in a liquid, semi-liquid or crystalline form. If crystalline, the crystals, coated or uncoated, may function as microcapsules and be dusted or loosely adhered to the balloon wall.

Microcapsules

The microcapsules usable in the invention may be fabricated in accordance with any of the known methods for preparing microcapsules. U.S. Pat. Nos. 4,897,268, 4,675,189, 4,542,025, 4,530,840, 4,389,330, 4,622,244, 4,464,317 and 4,943,449, the disclosures of which are incorporated herein by reference, describe methods for forming microcapsules which would be suitable for this invention. Microencapsulation is also described in *Encyclopedia of Poly. Sci. & Eng*, Vol. 9, by Curt Thies at pages 724-745 (2nd Ed. 1985) and in a chapter on Microencapsulation by R. E. Sparks in *Kirk-Othmer*, pages 470-493, Vol. 15 (3rd Ed).

The microcapsules of the invention may either be rupturable to release their contents or may be degradable such that they will open when left against the lumen walls. The capsules may release their contents through diffusion or by rupturing due to the application of ultrasonic forces. Many of the current applications for microcapsules require them to be easily ruptured under pressure, as in the case of carbonless copy paper. Typically, the microcapsules would be on the order of from 2 to 100 microns in diameter. The drug within the microcapsule will typically be in solution or otherwise dispersed throughout the polymer of the microcapsule. However, since it is possible to microencapsulate crystals, drug crystals may be employed. In such cases, the microcapsule may present sharp angles which will easily become embedded and fixed to the lumen wall when the balloon is inflated.

Brittle microcapsules will release their contents when the balloon is inflated since the expanding membrane of the balloon causes their walls to expand. In this manner, the fracture is inflation dependent, not time or pressure dependent. As the balloon inflates, encapsulated crystal tend to break free from their attachment to the balloon wall as it stretches. A typical dilatation catheter balloon may expand in circumference by 500% which stresses the attachment points to the microcapsules.

When referred to herein, "microcapsule" shall include microspheres. The release mechanisms from the microcapsules may include any of the existing release mechanisms, such as those described by Robert Langer in "New Methods of Drug Delivery", *Science*, Vol. 249, 28 September 1990, pp. 1527:1533.

Catheter formation

The dilatation catheters of the invention may include any dilatation catheter to which microcapsules are applied. The catheter need not be a dilation catheter as such. Any balloon catheter, whether capable of use in angioplasty or not may be employed. Since much lower pressures may be needed to release the drug, the balloon may be formed from a simple elastomer rather than a polyethylene. The microcapsules may be added in an original equipment manufacturing step or may be applied to previously formed catheters by spray coating or dipping the catheters to add microcapsules. A physician can thereby customize a catheter selected by adding a mixture of microcapsules containing the drugs needed to affect the lumen.

Figure 3:
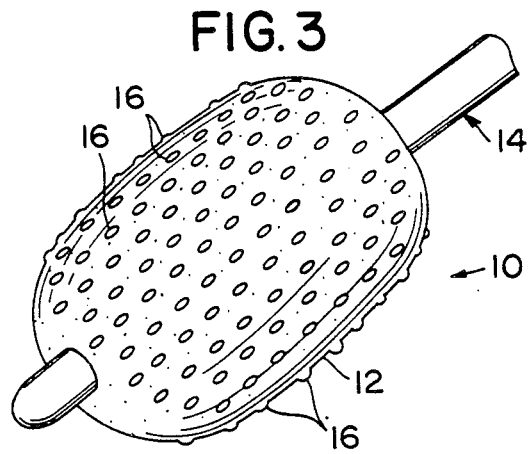
FIG. 3 is a view similar to that of FIG. 1 showing the balloon inflated.

FIGS. 1 and 3 show a portion of a typical balloon catheter 10 including a balloon 12. The balloon 12 is secured to the distal portion of a catheter tube 14 in a location overlying one or more apertures in the tube 14. The catheter 10 may include guiding means, insertion means or laser angioplasty means.

The balloon includes a covering of microcapsules 16 on its exterior surface. FIGS. 4 through 10 which are discussed below, provide details on the microcapsule attachment and release.

Figure 2:
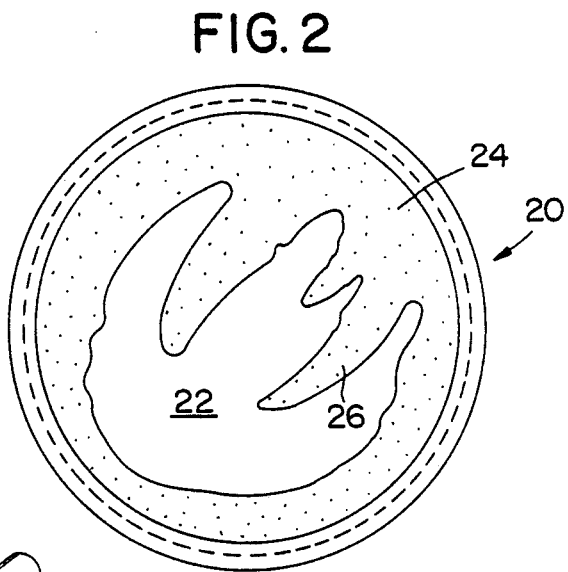
FIG. 2 is an enlarged transverse section of a body lumen in need of treatment.

The catheter 10 is inserted into the cardiovascular system until the balloon 12 is located at an occlusion site. A typical site is shown in FIG. 2. In that figure, a cross-section of a vessel 20 needing treatment is shown. The interior 22 of the vessel is largely occluded by plaque 24 which may include intimal flaps 26. The balloon 12 is inflated by the addition of pressurized fluid which unfolds the balloon presenting a relatively smooth outer surface or working profile for exerting radially outward forces on the plaque. This accomplishes vessel dilation which reduces the degree of occlusion by the plaque.

Unfortunately, the application of pressure against the vessel interior does not end the possibility of restenosis, or re-occlusion of the vessel at the treatment site. The balloon catheters 10 of the invention apply drugs or other agents directly to the vessel wall where needed. The microcapsules 16 which carry the active agents are placed directly against the plaque or other tissue of the vessel wall by the inflation of the balloon. The microcapsules release their contents through diffusion, breakage due to physical contact or ultrasound, degradation and the like. Where intimal flaps are present, the invention allows the placement of many microcapsules within the fissures that are normally difficult to reach and treat.

The catheters of the invention may also be prepared by inflating the balloon and dusting microcapsules over the balloon. When the balloon deflates the microcapsules remain attached in the pores of the balloon wall.

Treatment

The dilatation catheters of the invention are used following the routine catheterization procedures. However, due to the presence of the microcapsules, when the balloon is inflated microcapsules and the drugs contained therewithin are delivered to the lumen wall, especially to any fissured areas at the site being treated.

Figure 4:
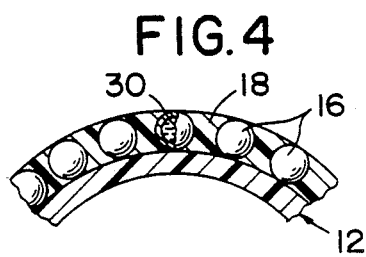
FIG. 4 is a greatly enlarged fragmentary section thereof as seen in FIG. 1.

FIG. 4 shows a fragment of the balloon 12 of FIG. 1. The balloon 12 is deflated in the Figure and traps the microcapsules 16 within a layer of adhesive 18. Although described as adhesive, layer 18 may simply be a portion of the balloon wall as a result of solvent bonding which overlays the microcapsules 16. One of the capsules 16 is shown in section to depict the interior filled with a liquid, semi-liquid or even crystalline agent 30. As shown, the microcapsules are firmly attached to the body of the deflated balloon 12.

Figure 6:
FIG. 6 is a greatly enlarged fragmentary section thereof showing dynamic mechanical function of the preferred form of the invention.
Figure 5:
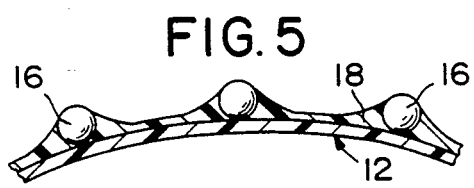
FIG. 5 is a greatly enlarged fragmentary section thereof as seen in FIG. 3.

In contrast, FIG. 5 is a fragmentary section of the inflated balloon 12 of FIG. 3 showing that inflation greatly stretches the balloon and adhesive 18 which exposes the microcapsules 16. The microcapsules are thus in a position that their contact with the vessel wall will cause them to release their contents to the cells of the vessel wall. Brittle microcapsules will rupture due to the stretching of the adhesive and not by the pressure of the balloon to the vessel wall. As the adhesive stretches it applies a force to the brittle microcapsules which causes them to rupture. FIG. 6 depicts the rupturing of a microcapsule 16. The agent inside is thus released directly against the cells of the vessel interior.

The amount of drug needed to treat the cells at a specific site in a vessel lumen is quite small. The microcapsules can easily carry the amount of cell affecting agents to the treatment site. A lower dosage is thus possible by the invention as well as a means to limit the possibly undesired effects of the drug on other areas of the body.

Figure 7:
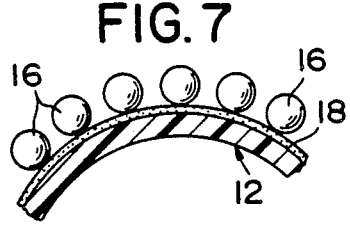
FIG. 7 is a greatly enlarged fragmentary section thereof showing a first alternate form of the invention.
Figure 9:
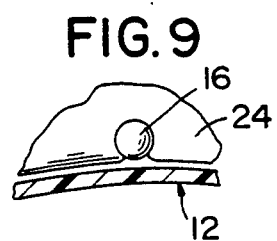
FIG. 9 is a greatly enlarged fragmentary section thereof showing dynamic mechanical function of a third alternate embodiment.

FIG. 7 shows an alternative form of the invention in which the microcapsules are attached to the balloon 12 by a thin layer of adhesive 18 in contrast to that shown in FIG. 4. In this form, the microcapsules may simply break free from the limited amount of adhesive allowing them to be pressed into placement where desired quite readily. The microcapsules of FIG. 7 may be made to release their contents over time after being embedded into the tissue of the vessel wall as shown in FIG. 9. This is in contrast to having the microcapsule break upon contact with the vessel wall.

Figure 8:
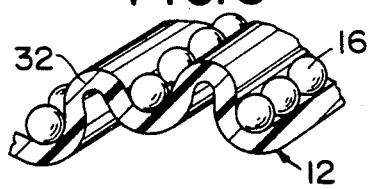
FIG. 8 is a greatly enlarged fragmentary pictorial detail of a second alternate form of the invention.
Figure 10:
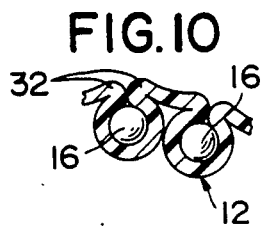
FIG. 10 is a greatly enlarged fragmentary section view thereof showing a fourth alternate form thereof.

FIGS. 8 and 10 show that the microcapsules 16 of the invention may simply be held in place mechanically between any folds 32, corrugations, cusps or the like. Such formations are common in deflated balloons and may be employed to carry the microcapsules without the need to attach the capsules by adhesive, welding or the like. As the balloon 12 inflates, the folds 32 are eliminated which expels the microcapsules into the treatment site.

The drawing of FIG. 10 shows that the balloon may be formed with permanent pleats that have a memory. In such a case, it is possible to place microcapsules 16 within the folds formed by the pleats as shown in FIG. 10. The application of more fluid into the balloon causes the pleats to unfold releasing the microcapsules 16.

If no microcapsules are present, such a design allows for a biphasic response, that is, the balloon may be partially inflated to be "fixed" against the lumen wall and finally inflated to a higher pressure where the lumen may be stretched.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. In a balloon angioplasty catheter of the type comprising a catheter body and a balloon positioned along the length of the catheter body, said balloon including means for remotely inflating and deflating said balloon; the improvement comprising:
   (a) a plurality of microcapsules on the exterior of said balloon, each of said microcapsules carrying a drug or combination of drugs for treatment or diagnostics within a body lumen when said catheter is positioned and inflated therewithin such that the drug or drugs may be released from said microcapsules.

2. The catheter of claim 1 wherein said drug or drugs are selected from the group consisting of restenosis limiting drugs, plaque deposition preventing drugs, anti-smooth muscle cell proliferation drugs and diagnostic dyes.

3. The catheter of claim 1 wherein said drug or drugs are selected from the group consisting of antiplatelet drugs, anticoagulant drugs, anti-inflammatory drugs, antimetabolite drugs and combinations of said drugs.

4. In a dilatation catheter of the type comprising a catheter body and a dilatation balloon positioned along the length of the catheter body; the improvement comprising:
   (a) a plurality of microcapsules on the exterior of said balloon, each of said microcapsules carrying a drug which may affect the interior of a lumen when said catheter is positioned and inflated therewithin such that said microcapsules rupture to release their contents.

5. The catheter of claim 4 wherein said drug or drugs are selected from the group consisting of restenosis limiting drugs, plaque deposition preventing drugs, anti-smooth muscle cell proliferation drugs and diagnostic dyes.

6. The dilatation catheter of claim 4 wherein said drug is selected from the group consisting of antiplatelet drugs, anticoagulant drugs, anti-inflammatory drugs, antimetabolite drugs and combinations of said drugs.

7. The dilatation catheter of claim 4 wherein said microcapsules are attached to said balloon surface by an adhesive.

8. The dilatation catheter of claim 4 wherein said microcapsules are attached to said balloon surface by solvent welding.

9. The dilatation catheter of claim 4 wherein said microcapsules are held to said balloon within folds of said balloon formed when said balloon is deflated.

10. In a dilatation catheter of the type comprising a catheter body and a dilatation balloon positioned along the length of the catheter body; the improvement comprising:
   (a) a plurality of microcapsules on the exterior of said balloon, each of said microcapsules carrying a drug which may affect the interior of a lumen when said catheter is positioned and inflated therewithin such that said microcapsules will release from said balloon upon inflation of said balloon.

11. The dilatation balloon catheter of claim 10 wherein said microcapsules carry a plaque-affecting chemical therewithin.

12. A method for limiting acute or chronic lumen closure in an animal lumen comprising the steps of:
   (a) inserting a dilatation catheter having a plurality of drug-containing microcapsules on the exterior of the catheter balloon into a lumen at the point where treatment is desired;
   (b) expanding said balloon against the walls of the lumen to break open and release the contents of the microcapsules against the lumen wall; and
   (c) removing said dilatation catheter.

13. A method for forming a balloon angioplasty catheter capable of supplying drug or drugs to a body lumen, said method comprising the steps of:
   (a) obtaining a catheter having a balloon; such that said drug is released onto a lumen during a balloon angioplasty procedure and
   (b) applying a plurality of drug-containing microcapsules to the exterior of said balloon.

14. The method of claim 13 wherein said step for applying microcapsules to said balloon consists of adhering microcapsules to said balloon.

15. The method of claim 13 wherein said step for applying microcapsules to said balloon consists of solvent welding microcapsules to said balloon.

16. The method of claim 13 wherein said step for applying microcapsules to said balloon consists of inflating said balloon and dusting drug-containing microcapsules onto said balloon and then deflating said balloon to trap said microcapsules in folds formed by the walls of said deflated balloon.

17. A method for treating the interior of a body lumen comprising the steps of:
   (a) inserting a balloon catheter having a balloon having an external coating of drug containing microcapsules into a lumen to be treated and positioning said balloon of said catheter next to the lumen wall needing treatment;
   (b) expanding said balloon against the lumen wall to cause said microcapsules to rupture and release their contents; and
   (c) removing said balloon catheter.

18. In a balloon angioplasty catheter of the type comprising a catheter body and a dilation balloon positioned along the length of the catheter body; the improvement comprising;
   (a) a releasable drug-carrying coating consisting of microcapsules in the exterior of said balloon, said drug of the type which may affect the interior of a lumen when said catheter is positioned and inflated therewithin in a balloon angioplasty procedure such that said coating is released from the balloon onto the lumen.

19. The dilatation catheter of claim 18 wherein said drug is selected from the group consisting of anti-smooth muscle cell proliferation drugs, antiplatelet drugs, anticoagulant drugs, anti-inflammatory drugs, anti-metabolite drugs and combinations of said drugs.

20. The dilatation catheter of claim 18 wherein said microcapsules are attached to said balloon surface by solvent welding.

21. The dilatation catheter of claim 18 wherein said microcapsules are attached to said balloon surface by an adhesive.

* * * * *